(12) United States Patent
Yu

(10) Patent No.: US 10,813,575 B2
(45) Date of Patent: Oct. 27, 2020

(54) DYNAMIC BLOOD GLUCOSE DATA ACQUIRING DEVICE AND HOST

(71) Applicant: GLUTALOR MEDICAL INC., Exton, PA (US)

(72) Inventor: Dongfang Yu, Guangdong (CN)

(73) Assignee: GLUTALOR MEDICAL INC., Exton, PA (US)

( * ) Notice: Subject to any disclaimer, the term of this patent is extended or adjusted under 35 U.S.C. 154(b) by 712 days.

(21) Appl. No.: 14/915,270

(22) PCT Filed: Oct. 27, 2014

(86) PCT No.: PCT/CN2014/089569
§ 371 (c)(1),
(2) Date: Feb. 29, 2016

(87) PCT Pub. No.: WO2016/065507
PCT Pub. Date: May 6, 2016

(65) Prior Publication Data
US 2016/0287150 A1    Oct. 6, 2016

(51) Int. Cl.
*A61B 5/145*     (2006.01)
*A61B 5/00*      (2006.01)
*A61B 5/1486*    (2006.01)

(52) U.S. Cl.
CPC ........ *A61B 5/14532* (2013.01); *A61B 5/0004* (2013.01); *A61B 5/14865* (2013.01);
(Continued)

(58) Field of Classification Search
None
See application file for complete search history.

(56) References Cited

U.S. PATENT DOCUMENTS

| 2,825,112 A | * | 3/1958 | Frieder | ..................... A42B 3/08 |
| | | | | 24/601.6 |
| 2003/0083619 A1 | * | 5/2003 | Angel | ............... A61M 5/14248 |
| | | | | 604/141 |

(Continued)

FOREIGN PATENT DOCUMENTS

| CN | 1845705 A | | 10/2006 |
| CN | 103630593 A | * | 3/2014 |

OTHER PUBLICATIONS

International Search Report of PCT Patent Application No. PCT/CN2014/089569 dated Jul. 17, 2015.

*Primary Examiner* — Kaylee R Wilson
*Assistant Examiner* — Jay B Shah
(74) *Attorney, Agent, or Firm* — The Belles Group, P.C.

(57) ABSTRACT

A dynamic blood glucose data acquiring device and a host are provided, wherein the collecting device comprises a portable host and a probe assembly; the probe assembly includes two glucolase micro electrode needles and a first circuit board; a first electrode terminal is provided on the first circuit board; the host includes an outer shell and a second circuit board which is located in the outer shell, and a second electrode terminal is provided on the second circuit board; the outer shell further includes a probe mounting position and a fixing structure; the probe assembly is mounted into the probe mounting position in such a way that the glucolase micro electrode needles are projected out of a lower surface of the outer shell; when the probe assembly is mounted into the probe mounting position, the first electrode terminal is electrically connected to the second electrode terminal.

20 Claims, 4 Drawing Sheets

(52) U.S. Cl.
CPC ............... *A61B 5/685* (2013.01); *A61B 5/72* (2013.01); *A61B 5/6833* (2013.01); *A61B 2562/08* (2013.01)

(56) References Cited

U.S. PATENT DOCUMENTS

| | | | | |
|---|---|---|---|---|
| 2006/0258959 | A1* | 11/2006 | Sode | A61B 5/14532 600/584 |
| 2011/0144463 | A1* | 6/2011 | Pesach | A61B 5/14532 600/345 |
| 2013/0092710 | A1* | 4/2013 | Bodet | B65D 83/425 222/402.2 |
| 2013/0102937 | A1* | 4/2013 | Ehrenreich | A61H 1/00 601/47 |

* cited by examiner

DYNAMIC BLOOD GLUCOSE DATA ACQUIRING DEVICE AND HOST

TECHNICAL FIELD

The present application relates to medical electronic technology field, and more particularly, relates to a dynamic blood glucose data acquiring device and a host.

BACKGROUND

For a diabetic, the monitoring of glucose is very important. By monitoring the glucose, it can be determine at what time the insulin should be injected in order to lower the glucose level in human body, or to supplement the glucose in order to make the glucose reach to a normal level.

At present, generally, a mainstream domestic portable blood glucose meter available in the market (for example, the products produced by companies such as Sanrupid, Omron, Yuwel, ACCU-CHEK, or the like) uses a blood sampling method which collects the peripheral blood of a human body for the detection of the blood glucose: firstly the subcutaneous tissue liquid of a human body of a user is collected using lancing devices or blood taking papers; then the blood glucose level is detected and determined by using a colorimetric method, an electrochemical method, or a photometer. However, when using the lancing device or blood taking papers to dynamically monitor the change of the blood glucose of a user, at least four blood glucose papers are needed every day, and the skin of the user needs to be pierced at least four times. In this way, the user may repeatedly feel stabbing pains, and the user experience is poor. Besides, the information about the blood glucose acquired by dynamically monitoring the blood glucose of the user by means of the paper is very limited, and it is impossible to analyze and determine the change of the blood glucose of the user with little blood glucose information.

Besides, it is possible to detect the glucose using an electrochemical sensor. In this case, the sensor is directly implanted into the blood vessels or the subcutaneous tissues of a patient. However, in general, these apparatuses are expensive, heavy and inflexible, and have larger volumes. Besides, the detection of the glucose using an electrochemical sensor needs to be carried out in a hospital or an office of a doctor, which greatly limits the activities of the patient.

It is also possible to use some apparatuses to detect the glucose with a sensor guiding object which is placed on the skin of the patient or the position near the skin. In this case, the sensor guiding object of this type may be bound on the body of the patient. However, the sensor guiding object of this type is usually heavy, and cannot be moved freely. Furthermore, the sensor guiding object or the sensor includes cables or wires which are configured to connect the sensor to other apparatuses for the purpose of transmitting signals from the sensor to an analyzer. The size of the sensor guiding object and the present of the cables and wires also limit the activities of the patient.

BRIEF SUMMARY

The object of the present application is to provide a dynamic blood glucose data acquiring device and a host, aiming at the defects in the art that the collection of the blood glucose is fussy, and cables are needed for the transmission of the signals collected.

The technical solutions to solve the technical problem are as follows.

In one aspect, a dynamic blood glucose data acquiring device is provided, which comprises a portable host and a probe assembly; wherein the probe assembly includes two glucose probes, and a first circuit board which is configured to process signals from the glucose probes; a first electrode terminal is provided on the first circuit board; the host includes an outer shell and a second circuit board which is located in the outer shell, and a second electrode terminal is provided on the second circuit board; the outer shell further includes a probe mounting position and a fixing structure for fixing the outer shell to a human body; the probe assembly is mounted into the probe mounting position in such a way that the glucose probes are projected out of a lower surface of the outer shell; when the probe assembly is mounted into the probe mounting position, the first electrode terminal on the first circuit board is electrically connected to the second electrode terminal on the second circuit board.

In one embodiment, a battery configured for supplying power to the second circuit board is arranged on the second circuit board, and the second circuit board further supplies power to the first circuit board via the second electrode terminal and the first electrode terminal.

In this embodiment, the outer shell of the host includes an upper shell and a lower shell which are buckled into each other; the second circuit board is fixed in a space formed by the upper shell and the lower shell; a Bluetooth communication module is provided on the second circuit board.

In this embodiment, a tail of each of the glucose probes is welded on the first circuit board and is perpendicular to the first circuit board; when the probe assembly is assembled to the probe mounting position on the outer shell of the host, each of the glucose probes is perpendicular to the surface of the outer shell.

In this embodiment, the probe assembly includes a piston subassembly and an elastic element, and the first circuit board is fixedly mounted on the piston subassembly; one side of the elastic element is electrically connected to the first electrode terminal on the first circuit board, and the other side of the elastic element is located on the periphery of the piston subassembly; the probe mounting position on the outer shell is a through-hole running through the upper shell and the lower shell, and a diameter of the through-hole matches with a diameter of the piston subassembly; a contact elastic sheet is arranged in a position on the through-hole corresponding to the elastic element of the probe assembly, and the contact elastic sheet is electrically connected to the second electrode terminal of the second circuit board.

In this embodiment, the through-hole on the outer shell of the host is formed by a piston sleeve, and piston sleeve is received between the upper shell and the lower shell; the contact elastic sheet is fixed on the piston sleeve.

In this embodiment, a radial rib is formed on the periphery of the piston subassembly; a radial positioning groove is defined on a position on the inner wall of the piston sleeve corresponding to the radial rib of the piston subassembly; or a radial positioning groove is defined on the periphery of the piston subassembly, and a radial rib is formed on a position on the inner wall of the piston sleeve corresponding to the radial positioning groove.

In this embodiment, the fixing structure on the outer shell includes an adhesive back patch engaged with the bottom of the lower shell, and a through-hole configured for the glucose probe to run through is further defined on the adhesive back patch.

Preferably, a diameter of the through-hole is less than a diameter of the piston subassembly.

In another aspect, a host for a dynamic blood glucose date acquiring device is further provided, which comprises an outer shell and a second circuit board which is located in the outer shell, and a second electrode terminal is provided on the second circuit board; the outer shell further includes a probe mounting position and a fixing structure for fixing the outer shell to a human body; an electrode terminal configured to connect the probe assembly to the second circuit board is arranged in the probe mounting position.

In the dynamic blood glucose data acquiring device and a host according to the present application, the probe assembly is fixed on the human body via the portable host, and the blood glucose signals are acquired via the glucose probes of the probe assembly; in this way, the acquiring, the processing and the output of the blood glucose signals can be achieved. In the present application, the blood glucose detection data may be transmitted to a terminal device via Bluetooth, which greatly facilitating the acquiring and the analysis of the blood glucose data, thereby providing a reliable basis for the diagnosis of a doctor or an expert.

DETAILED DESCRIPTION OF THE PREFERRED EMBODIMENT

To make the object, the technical solution and the technical advantages more clearly, the present application will be further described with reference to the accompanying drawings and embodiments in the following. It should be understood that, the specific embodiment described here is just for explanation, not for limitation.

Figure 1:
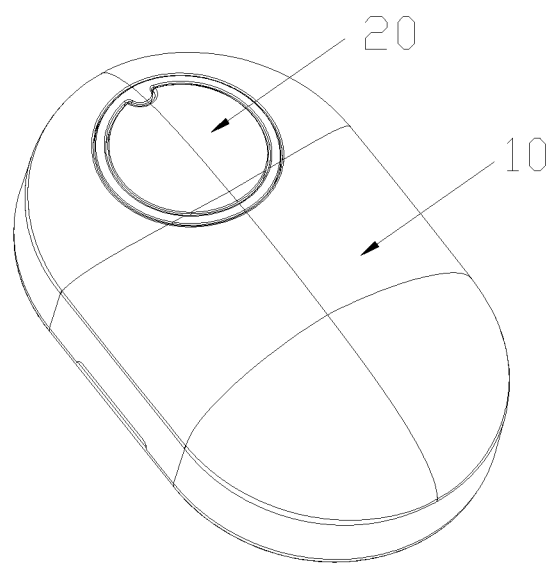
FIG. 1 is a schematic view of a dynamic blood glucose data acquiring device according to an embodiment of the present application.
Figure 2:
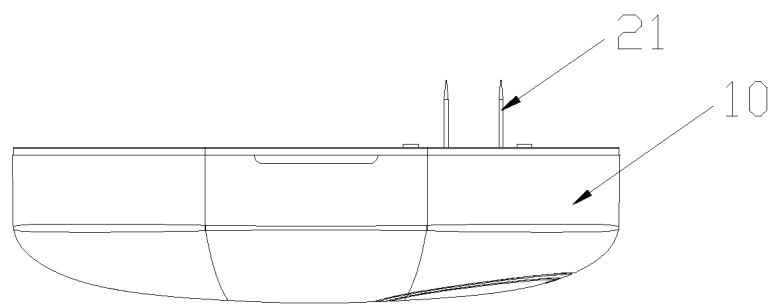
FIG. 2 is a side view of the dynamic blood glucose data acquiring device shown in FIG. 1.
Figure 3:
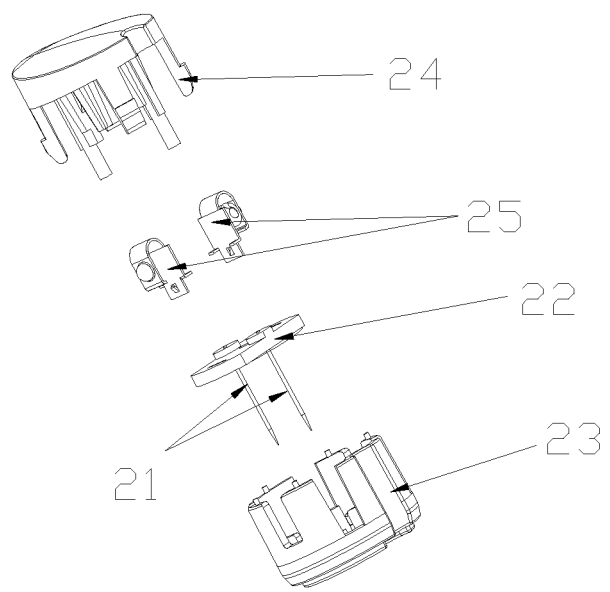
FIG. 3 is a schematic view of the probe assembly of the dynamic blood glucose data acquiring device shown in FIG. 1.
Figure 4:
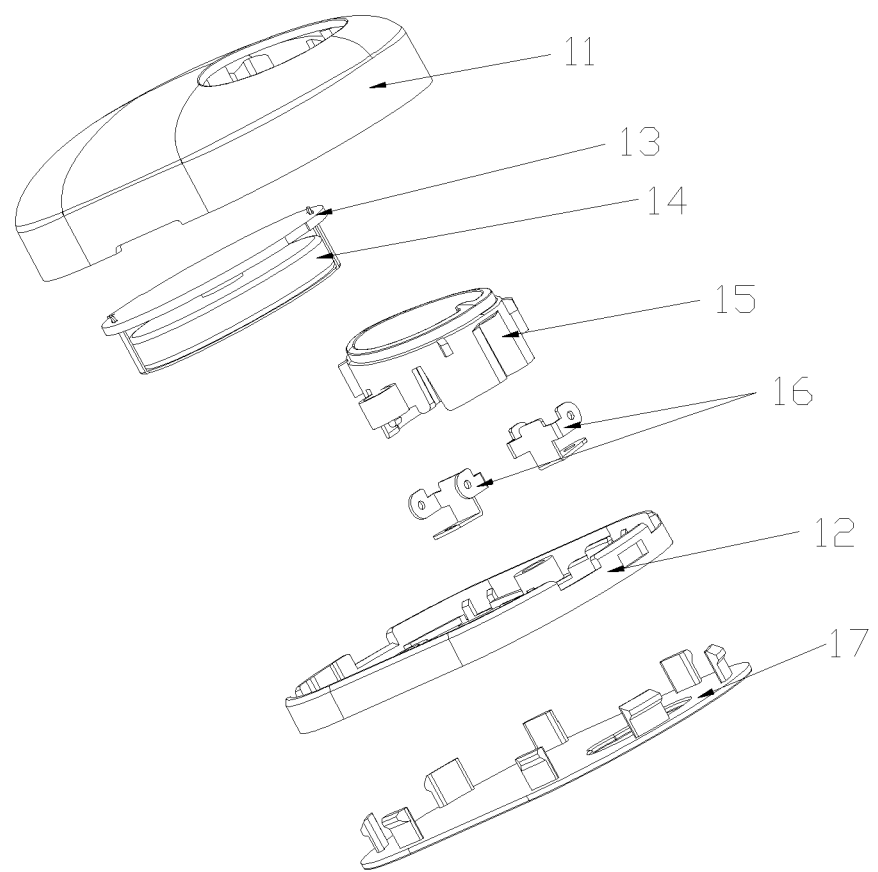
FIG. 4 is a schematic view of the host of the dynamic blood glucose data acquiring device shown in FIG. 1.
Figure 5:
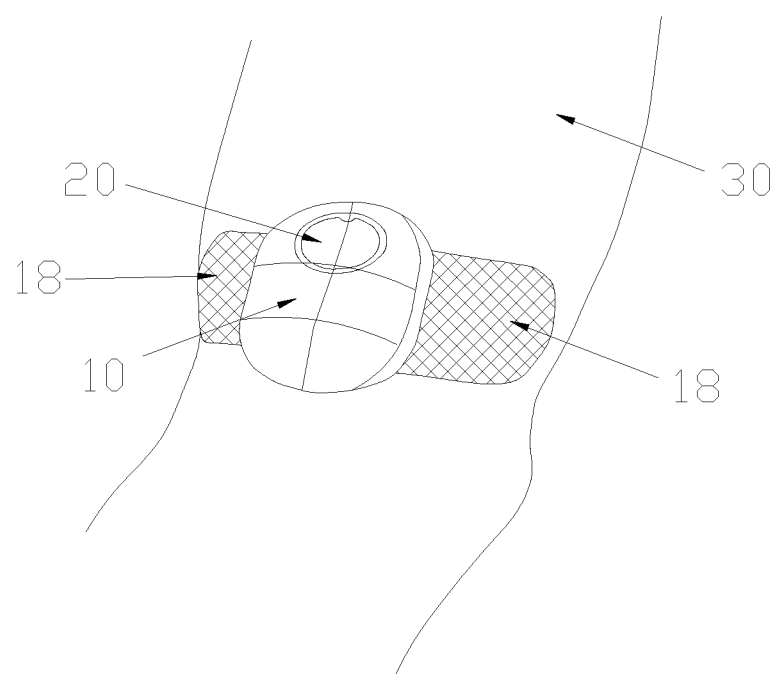
FIG. 5 is a view in which the dynamic blood glucose data acquiring device shown in FIG. 1 is worn.

FIGS. 1-5 show a dynamic blood glucose data acquiring device according to an embodiment of the present application. The dynamic blood glucose data acquiring device can be worn on an arm 30 of a human body, for the purpose of continuously collecting blood glucose data of the human body. In this embodiment, the dynamic blood glucose data acquiring device comprises a portable host 10 and a probe assembly 20. In this case, the probe assembly 20 includes two glucose probes 21, and a first circuit board 22 which is configured to process signals from the glucose probes. Besides, a first electrode terminal is provided on the first circuit board 22. The host 20 includes an outer shell and a second circuit board 13 which is located in the outer shell, and a second electrode terminal is provided on the second circuit board 13. The outer shell further includes a probe mounting position and a fixing structure for fixing the outer shell to the human body. The probe assembly 20 is mounted into the probe mounting position in such a way that the glucose probes 21 are projected out of a lower surface of the outer shell. When the probe assembly 20 is mounted into the probe mounting position, the first electrode terminal on the first circuit board 22 is electrically connected to the second electrode terminal on the second circuit board 13.

The glucose probe 21 in this case has a length of 4.9 mm, which is capable of piercing the cuticle and epidermis, and further reaching to the corium layer. Oxidation reactions occur between the glucose probe 21 and the glucose in the human body, thereby forming electrical signals (including low-voltage and low-current signals). The first circuit board 22 is integrated with a micro processor. The micro processor is configured to preliminarily process (such as filter, amplify, or the like) the electrical signals from the glucose probe 21, and send the processed electrical signals to the second circuit board 13 via the first electrode terminal and the second electrode terminal. The second circuit board 13 is integrated with a MCU, and converts the electrical signals from the probe assembly 20 into blood glucose readings via the MCU.

Since an effective time of the glucose probe 21 is 7 days (that is, the glucose probe 21 is capable of steadily reacting with the glucose in the human body within 7 days), it is possible for the probe assembly 20 in the dynamic blood glucose data acquiring device to continuously collect the blood glucose data for 7 days in real time in principle, and the host 10 carries out the conversion of the blood glucose data, thereby the dynamic blood glucose data of the human body is acquired. Certainly, for the accuracy of the blood glucose data collecting and the comfort of wearing, it is possible to limit a valid period of the probe assembly 20 within 5 days.

Besides, since the probe assembly 20 is assembled to the host 10, it is possible to disassemble the probe assembly 20 from the host 10 and use a new probe assembly 20 to collect the blood glucose data combing with the host, after the probe assembly 20 becomes invalid (for example, after the probe assembly 20 has been used for 7 days). Therefore, with the structure described above, the probe assembly 20 is possible to be used as a disposable product, and thus the glucose probe 21 implanted into the human body is avoided from being repeatedly used. However, the host 10 may be repeatedly used in order to avoid waste.

The second circuit board 13 includes a battery 14 configured for supplying power to the second circuit board 13. The second circuit board 13 further supplies power to the first circuit board 22 via the second electrode terminal and the first electrode terminal. The battery 14 may be a chargeable lithium cell, and a charging interface may be provided on the second circuit board 13. The battery 14 may also be a button cell which is convenient to change.

The outer shell of the host 10 includes an upper shell 11 and a lower shell 12 which are buckled into each other. The second circuit board 13 is fixed in a space formed by the upper shell 11 and the lower shell 12. A tail of each of the glucose probes 21 is welded on the first circuit board 22 and is perpendicular to the first circuit board 22. When the probe assembly 20 is assembled to the probe mounting position on the outer shell of the host 10, each of the glucose probes 21 is perpendicular to the surface of the outer shell (that is, the lower shell 12). In this way, it is possible for the glucose probe 21 to be perpendicularly inserted into the epidermis of the human body. Certainly, in the practical application, the glucose probe 21 of the probe assembly 20 may be obliquely inserted into the epidermis of the human body.

The probe assembly 20 includes a piston subassembly and an elastic element 25; wherein the piston subassembly is an assembly of a piston upper shell 24 and a piston lower shell 23, and the first circuit board 22 is fixedly mounted via the piston upper shell 24 and the piston lower shell 24. One side of the elastic element 25 is electrically connected to the first electrode terminal on the first circuit board 22, and the other side of the elastic element 25 is located on the periphery of the piston subassembly. The probe mounting position on the outer shell of host 10 is a through-hole running through the upper shell and the lower shell, and a diameter of the through-hole matches with a diameter of the piston subassembly. A contact elastic sheet 16 is arranged in a position on the inwall of the through-hole of the outer shell of the host 10 corresponding to the elastic element 25 of the probe assembly 20, and the contact elastic sheet 16 is electrically connected to the second electrode terminal of the second circuit board 13. In this way, when the probe assembly 20 is assembled to the host 10, the first circuit board 22 is electrically connected to the second circuit board 13 by contacting the elastic element 25 with the contact elastic sheet 16.

In particular, the through-hole on the outer shell of the host 10 is formed by a piston sleeve 15, and the contact elastic sheet 16 is fixed on the piston sleeve. The piston sleeve 15 is received between the upper shell 11 and the lower shell 12, and an inner diameter of the piston sleeve 15 matches with an outer diameter of the piston subassembly of the probe assembly 20. In this way, it is possible for the probe assembly 20 to be directly inserted into the piston sleeve 15 in order to achieve an assembly thereof. A buckle component may be arranged on the periphery of the piston subassembly and an inner wall of the piston sleeve 15, in order to prevent the probe assembly 20 which is inserted into the piston sleeve 15 from getting out of the piston sleeve 15. It is also possible to provide a component configured to prevent the probe assembly 20 from getting out of the piston sleeve 15 (such as, a structure similar to a buckle or a barb) between the piston subassembly of the probe assembly 20 and the piston sleeve 15 of the host 10.

When using the dynamic blood glucose data acquiring device of the present application, the host 10 is firstly fixed on the human body (such as an arm), and the piston subassembly of the probe assembly 20 is in turn inserted into the piston sleeve 15 of the host 10, such that the glucose probe 21 pierces into the skin, and thus the collection of the blood glucose data can be achieved.

Certainly, in the practical application, it is also possible for the probe mounting position on the host 10 to be a recess on the bottom of the host 10. When using the dynamic blood glucose data acquiring device of the present application, the probe assembly 20 is firstly fixed on the human body, that is, the glucose probe 21 pierces into the skin; then the host 10 is fixed on the human body with the recess on the bottom of the host 10 aligned with the tail of the probe assembly 20. Compared with the method using the through-hole, the wearing of the probe mounting position in form of a recess is complicated, and it is not easy to control the piercing of the glucose probe 21 into the skin.

In order to achieve a precise assembly of the probe assembly 20, a radial rib may be formed on the periphery of the piston subassembly. Accordingly, a radial positioning groove is defined on a position on the inner wall of the piston sleeve 15 corresponding to the radial rib of the piston subassembly. The assembly of the probe assembly 20 may be achieved only by inserting the radial rib into the radial positioning groove. Certainly, it is also possible for the radial positioning groove to be defined on the periphery of the piston subassembly, and for the radial rib to be formed on a position on the inner wall of the piston sleeve 15 corresponding to the radial positioning groove. In this way, the precise assembly of the probe assembly 20 may also be achieved.

The fixing structure on the outer shell of the host 10 includes an adhesive back patch 17 engaged with the bottom of the lower shell, and a through-hole configured for the glucose probe 21 to run through is further defined on the adhesive back patch 17. A medical tape 18 having a mesh may be fixed on the adhesive back patch 17, and the adhesive back patch 17 is further adhered to the human body via the medical tape 18. The medical tape has a good permeability, and will not bring about irritability or uncomfortable symptoms after being used for a long time.

In particular, a diameter of the through-hole of the adhesive back patch 17 is less than a diameter of the piston subassembly of the probe assembly 20. In this way, during the disassembly of the probe assembly 20, the probe assembly 20 may be directly pushed to move in an inserting direction, and the adhesive back patch 17 may be separated from the lower shell 12 of the host 10 when the probe assembly 20 is getting out of the piston sleeve 15. Therefore, the wearing thereof is hygienic.

In order to send out the blood glucose data of the host 10, a Bluetooth communication module may be provided on the second circuit board 13. In this way, any apparatus having a function of Bluetooth communication, such as a cell-phone, a laptop or the like, may be communicated with the host 10 via Bluetooth, and may further collect the blood glucose data acquire d.

Those are preferred embodiments of the present application. However, it should be understood that, the protection scope of the present application is not limited here. In the inspiration of the present application, one skilled in the art may easily make various modifications and equivalents, without going beyond the scope the claims intend to protect of the present application. All these belong to the protection of the present application should be protected. Therefore, the protection scope of the present application is subjected to the protection scope claimed in claims.

The invention claimed is:

1. A dynamic blood glucose data acquiring device comprising:
  a portable host and a probe assembly removably connected to the portable host;
  wherein the probe assembly includes two glucose probes and a first circuit board which is configured to process signals from the two glucose probes, the two glucose probes being coupled directly to the first circuit board, a first electrode terminal is provided on the first circuit board;
  the portable host includes an outer shell and a second circuit board located in the outer shell, the second circuit board comprising a second electrode terminal, and wherein the outer shell is configured to hold the probe assembly, the outer shell comprising a housing and an adhesive back patch detachably coupled to the housing for fixing the portable host to a human body with the adhesive back patch adjacent to the human body;
  wherein the probe assembly is mounted into the outer shell in such a way that the glucose probes are projected out of a lower surface of the outer shell, and wherein when the probe assembly is mounted into the outer shell, the first electrode terminal on the first circuit board is electrically connected to the second electrode terminal on the second circuit board;

the probe assembly comprising a subassembly and a first elastic piece, the subassembly comprising an upper shell and a lower shell that are coupled together, and the first circuit board is fixedly mounted in a cavity formed between the upper shell and the lower shell, one side of the first elastic piece is electrically connected to the first electrode terminal on the first circuit board, and another side of the first elastic piece is located on a periphery of the subassembly;

the housing of the outer shell of the portable host comprising a first through-hole extending through the housing from a first opening in a top surface of the housing to a second opening in the bottom surface of the housing, the first through-hole forming a continuous passageway through the housing from the top surface of the housing to the bottom surface of the housing;

the adhesive back patch of the outer shell of the portable host comprising a second through-hole extending through the adhesive back patch, the adhesive back patch being adjacent to the bottom surface of the housing and the second through-hole being aligned with the first through-hole, a first diameter of the first through-hole being greater than a second diameter of the second through-hole;

wherein the subassembly of the probe assembly is inserted through the first opening in the top surface of the housing of the portable host and into the first through-hole to detachably couple the probe assembly to the portable host, the first diameter of the first through-hole matching with a third diameter of the subassembly so that the subassembly nests within the first through-hole, and wherein the third diameter of the subassembly is greater than the second diameter of the second through-hole so that the subassembly cannot extend into and through the second through-hole of the adhesive back patch; and wherein a second elastic piece that is electrically connected to the second electrode terminal of the second circuit board is arranged on an inner wall of the first through-hole in a position that corresponds to the first elastic piece of the probe assembly so that when the probe assembly nests within the first through-hole of the outer shell of the portable host the first elastic piece contacts with the second elastic piece to electrically connect the first circuit board to the second circuit board.

2. The dynamic blood glucose data acquiring device according to claim 1, wherein a battery configured for supplying power to the second circuit board is arranged on the second circuit board, and the second circuit board further supplies power to the first circuit board via the second electrode terminal and the first electrode terminal.

3. The dynamic blood glucose data acquiring device according to claim 1, wherein the housing of the outer shell of the portable host includes an upper shell and a lower shell which are buckled into each other, and the first through-hole runs through the upper shell and the lower shell; the second circuit board is fixed in a space formed by the upper shell and the lower shell; a Bluetooth communication module is provided on the second circuit board.

4. The dynamic blood glucose data acquiring device according to claim 3, wherein a tail of each of the glucose probes is welded on the first circuit board and is perpendicular to the first circuit board; when the probe assembly is assembled to the outer shell of the portable host, each of the glucose probes is perpendicular to a lower surface of the outer shell.

5. The dynamic blood glucose data acquiring device according to claim 3, wherein the portable host further includes a piston sleeve located in the housing and defining the first through-hole, and the piston sleeve is received between the upper shell and the lower shell of the housing of the outer shell of the portable host; the second elastic piece is fixed on the piston sleeve.

6. The dynamic blood glucose data acquiring device according to claim 5, wherein:

a radial rib is formed on the periphery of the piston subassembly and a radial positioning groove is defined on a position on the inner wall of the first through-hole which is defined by the piston sleeve, the position on the inner wall corresponding to a position of the radial rib of the subassembly; or a radial positioning groove is defined on the periphery of the subassembly, and a radial rib is formed on a position on the inner wall of the first through-hole which is defined by the piston sleeve, the position on the inner wall corresponding to a position of the radial positioning groove.

7. The dynamic blood glucose data acquiring device according to claim 3, wherein the adhesive back patch is engaged with a bottom surface of the lower shell of the housing of the outer shell of the portable host.

8. The blood glucose data acquiring device according to claim 1 wherein a top surface of the upper shell of the subassembly of the probe assembly remains exposed through the first opening in the top surface of the housing of the portable host when the probe assembly nests within the first through-hole of the housing of the portable host.

9. A host for a dynamic blood glucose data acquiring device comprising:

a housing that defines a cavity, a circuit board located in the cavity;

wherein the housing comprises a first through-hole extending from a first opening in a top surface of the housing to a second opening in a bottom surface of the housing, the first through-hole forming a continuous passageway through the housing from the top surface of the housing to the bottom surface of the housing, the first through-hole having a first diameter and being configured to receive and detachably hold a probe assembly;

an adhesive back patch detachably coupled to the housing to at least partially cover the bottom surface of the housing, the adhesive back patch comprising a second through-hole that is aligned with the first through-hole, the second through-hole having a second diameter that is less than the first diameter so that a housing of the probe assembly cannot fit into the second through-hole; and wherein the adhesive back patch is configured to be adhered to a human body with medical tape so that glucose needles of the probe assembly penetrate into a skin of the human body when the probe assembly is positioned in the first through-hole of the housing.

10. The host according to claim 9, wherein the housing further comprises an upper shell and a lower shell which are coupled together, and the first through-hole runs through the upper shell and the lower shell, and wherein a Bluetooth communication module is provided on the second circuit board.

11. The host according to claim 10, where further comprising a piston sleeve located in the cavity of the housing and defining the first through-hole, wherein the piston sleeve is received between the upper shell and the lower shell.

12. The host according to claim 10, wherein the adhesive back patch is engaged with the bottom surface of the housing which is formed by of the lower shell, and wherein the glucose needles of the probe assembly are configured to extend through the second through-hole while the housing of the probe assembly is prevented from passing into the second through-hole.

13. The host according to claim 9, further comprising a battery configured for supplying power to the second circuit board and arranged on the second circuit board, and wherein the second circuit board is configured to supply power to a first circuit board of the probe assembly when the probe assembly is detachably held within the first through-hole of the housing.

14. The host according to claim 9, further comprising:
   a radial positioning groove formed into an inner wall of the housing that surrounds the first through-hole, the radial positioning groove being configured to receive a radial rib located on a periphery of the housing of the probe assembly; or
   a radial rib located on the inner wall of the housing that surrounds the first through-hole, the radial rib being configured to engage a radial positioning groove defined on the periphery of the housing of the probe assembly.

15. A blood glucose data acquiring device comprising:
   a portable host comprising an outer shell comprising a second housing and a backer panel, the second housing comprising a top surface, a bottom surface, and cavity, a second circuit board located in the cavity of the second housing, a first through-hole extending through the first housing from a first opening in the top surface of the second housing to a second opening in the bottom surface of the second housing, the first through-hole forming a continuous passageway through the second housing from the top surface of the second housing to the bottom surface of the second housing, the first through-hole having a first diameter;
   the backer panel detachably coupled to the second housing to at least partially cover the bottom surface of the second housing, the backer panel comprising a second through-hole having a second diameter that is less than the first diameter;
   a probe assembly comprising a first housing comprising a top surface, a bottom surface, and a cavity, a first circuit board located in the cavity of the first housing, and two glucose needles operably coupled to the first circuit board and protruding from the bottom surface of the first housing, the first housing having a third diameter that is greater than the second diameter so that the first housing does not fit into or through the second through-hole in the backer panel; and
   wherein the portable host is configured to be placed on skin of a user with the backer panel adjacent to the skin, and wherein the probe assembly is positioned in the first through-hole of the second housing of the portable host to detachably couple the probe assembly to the portable host by inserting the probe assembly through the first opening in the top surface of the second housing of the portable host, the two glucose needles extending through the second through-hole in the backer panel and into the skin of the patient to monitor a glucose level of the patient, and wherein the first and second circuit boards are operably coupled together when the probe assembly is coupled to the portable host.

16. The blood glucose data acquiring device according to claim 15 wherein the portable host is a reusable component and the probe assembly is a disposable assembly, and wherein the probe assembly is detached from the portable host by pushing the portable host towards the skin while detaching the second housing of the portable host from the backer panel, whereby the probe assembly passes through the second opening in the bottom surface of the second housing of the portable host during detachment of the probe assembly from the portable host.

17. The blood glucose data acquiring device according to claim 15 further comprising:
   the portable host comprising a first contact element electrically connected a second electrode terminal of the second circuit port, a portion of the first contact element positioned on an inner wall of the first through-hole of the second housing of the portable host;
   the probe assembly comprising a second contact element electrically connected to a first electrode terminal of the first circuit board, a portion of the second contact element located on a periphery of the first housing of the probe assembly; and
   wherein when the probe assembly is detachably coupled to the portable host, the portion of the second contact element contacts the portion of the first contact element to operably couple the first circuit board to the second circuit board.

18. The blood glucose data acquiring device according to claim 15 further comprising:
   at least one of a radial rib or a radial groove located on a periphery of the first housing of the probe assembly;
   the other one of the radial rib or a radial groove located on an inner wall of the first through-hole of the second housing of the portable host; and
   wherein the probe assembly can only be inserted through the first opening in the top surface of the second housing of the portable host when the at least one of the radial rib or the radial groove located on the periphery of the first housing of the probe assembly is aligned with the other one of the radial rib or the radial groove located on the inner wall of the first through-hole of the second housing of the portable host.

19. The blood glucose data acquiring device according to claim 15 wherein the two glucose needles are coupled directly to the first circuit board such that a tail of the two glucose needles is in direct contact with the first circuit board.

20. The blood glucose data acquiring device according to claim 15 wherein the top surface of the first housing of the probe assembly is exposed through the first opening in the top surface of the second housing when the probe assembly is coupled to the portable host.

* * * * *